US010792512B1

(12) United States Patent
De Souza et al.

(10) Patent No.: US 10,792,512 B1
(45) Date of Patent: Oct. 6, 2020

(54) METALLIC MODULES AND ASSEMBLY SYSTEM FOR THE FORMATION OF SHIELDED WALLS, FLOOR AND CEILING FOR ROOMS USED FOR RADIOTHERAPY

(71) Applicants: Pedro Kahn Machado De Souza, Rio de Janeiro (BR); Sergio Kahn Machado De Souza, Rio de Janeiro (BR)

(72) Inventors: Pedro Kahn Machado De Souza, Rio de Janeiro (BR); Sergio Kahn Machado De Souza, Rio de Janeiro (BR)

( * ) Notice: Subject to any disclaimer, the term of this patent is extended or adjusted under 35 U.S.C. 154(b) by 0 days.

(21) Appl. No.: 16/539,030

(22) Filed: Aug. 13, 2019

(51) Int. Cl.
*A61N 5/10* (2006.01)
*G21F 1/08* (2006.01)

(52) U.S. Cl.
CPC ............... *A61N 5/10* (2013.01); *G21F 1/08* (2013.01); *A61N 2005/1094* (2013.01)

(58) Field of Classification Search
CPC ..... G21F 3/04; G21F 3/00; G21F 7/00; G21F 1/04; E04B 2/08; E04B 1/92; E04B 2001/925; E04B 1/34315; E04B 2002/0267; A61N 2005/1094
USPC ................................ 250/515.1, 517.1, 518.1
See application file for complete search history.

(56) References Cited

U.S. PATENT DOCUMENTS

| | | | | |
|---|---|---|---|---|
| 4,876,593 A * | 10/1989 | Bauer | ...................... | G21F 7/03 348/83 |
| 5,009,836 A * | 4/1991 | Grimm | ................... | G21C 19/00 376/260 |
| 5,241,573 A * | 8/1993 | Thacker | .................... | G21F 3/04 250/517.1 |
| 5,633,508 A * | 5/1997 | Schleppenbach | ......... | G21F 1/02 250/515.1 |
| 5,958,557 A * | 9/1999 | Naor | ....................... | H01Q 1/42 250/515.1 |
| 6,606,835 B1 * | 8/2003 | Bilka | ....................... | E04B 2/06 52/311.1 |
| 8,689,509 B2 * | 4/2014 | Gleeson | .................. | E04B 2/707 52/461 |
| 8,820,024 B1 * | 9/2014 | Abdullah | .................. | E04B 2/08 52/561 |
| 9,183,957 B2 * | 11/2015 | Farrell | ...................... | G21F 3/00 |
| 9,404,234 B2 * | 8/2016 | Jain | ........................ | E02D 27/32 |

(Continued)

*Primary Examiner* — David A Vanore
(74) *Attorney, Agent, or Firm* — Scott Houtteman; Houtteman Law LLC

(57) ABSTRACT

A modular structure is disclosed that shields people from radiation typically encountered in radiotherapy rooms. The structure can be easily assembled without cracks. Moreover, the structure can be assembled and repaired quickly, without interrupting treatments for long periods of time. The structure is made of two general types of modules. A base module is made up of two cuboids fused along facing long edges and offset, one from the other, both vertically and horizontally. A complementary module is made of a single flatter shaped cuboid. It is designed to fill gaps that appear at the top and bottom of the assembled array of base modules. These modules, as configured, allows several structures to be assembled by quick and simple fitting and horizontal and vertical stacking of the modules. The modules can be manufactured from low cost materials such as metal casing filled with metal powder.

3 Claims, 8 Drawing Sheets

(56) References Cited

U.S. PATENT DOCUMENTS

| | | | |
|---|---|---|---|
| 2010/0294960 A1* | 11/2010 | Frank | G21F 3/04 |
| | | | 250/517.1 |
| 2013/0175461 A1* | 7/2013 | Lambert | G21F 3/00 |
| | | | 250/517.1 |
| 2018/0110666 A1* | 4/2018 | Yim | E04H 3/08 |
| 2018/0258659 A1* | 9/2018 | LeBlanc | G21F 3/04 |
| 2019/0316294 A1* | 10/2019 | Medoff | C10L 1/026 |

\* cited by examiner

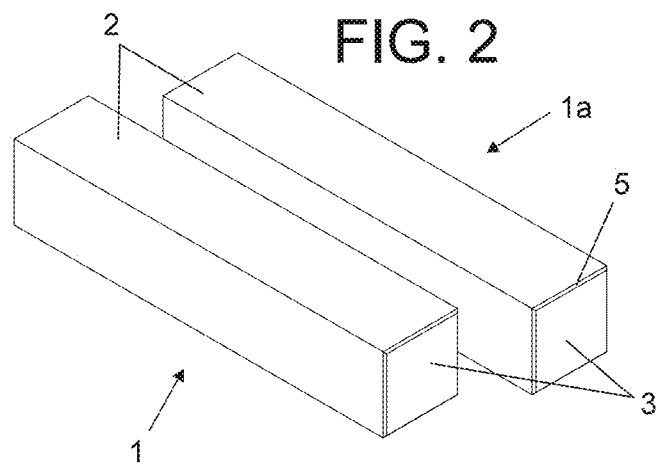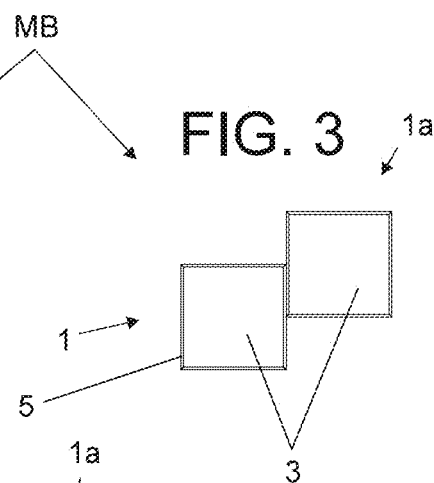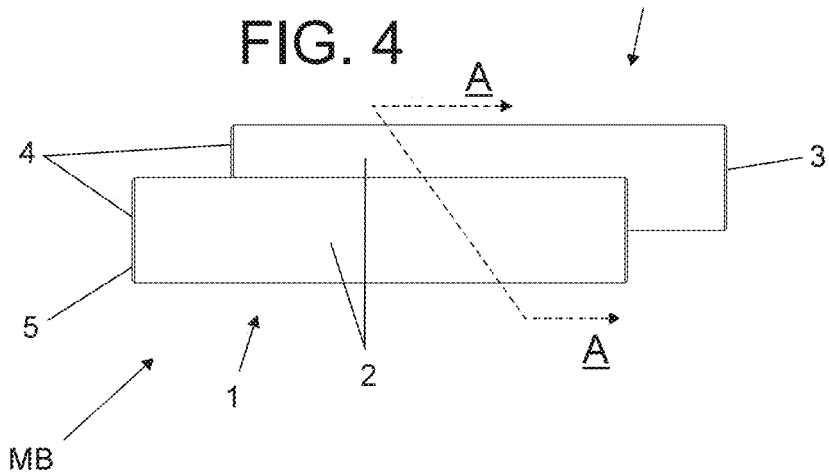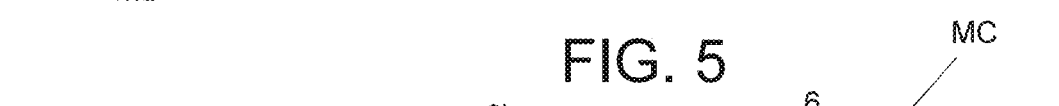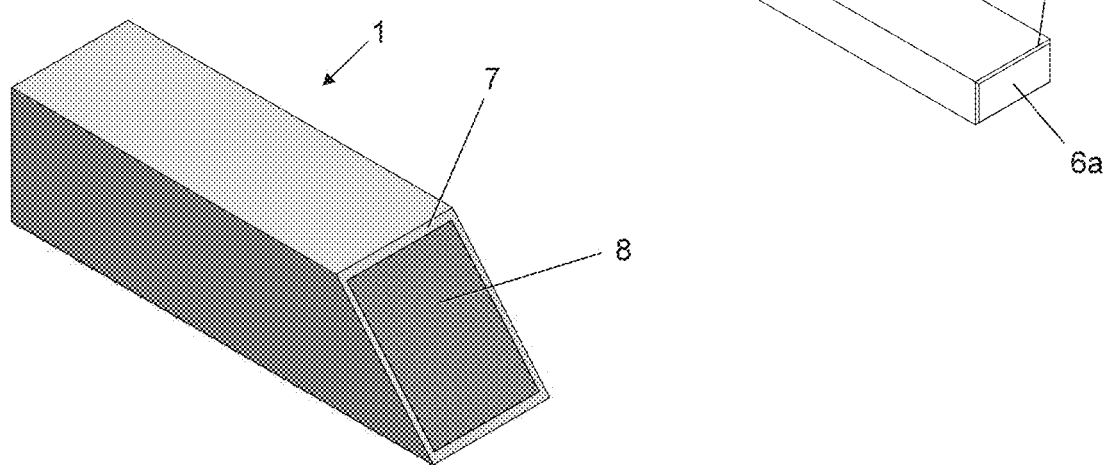

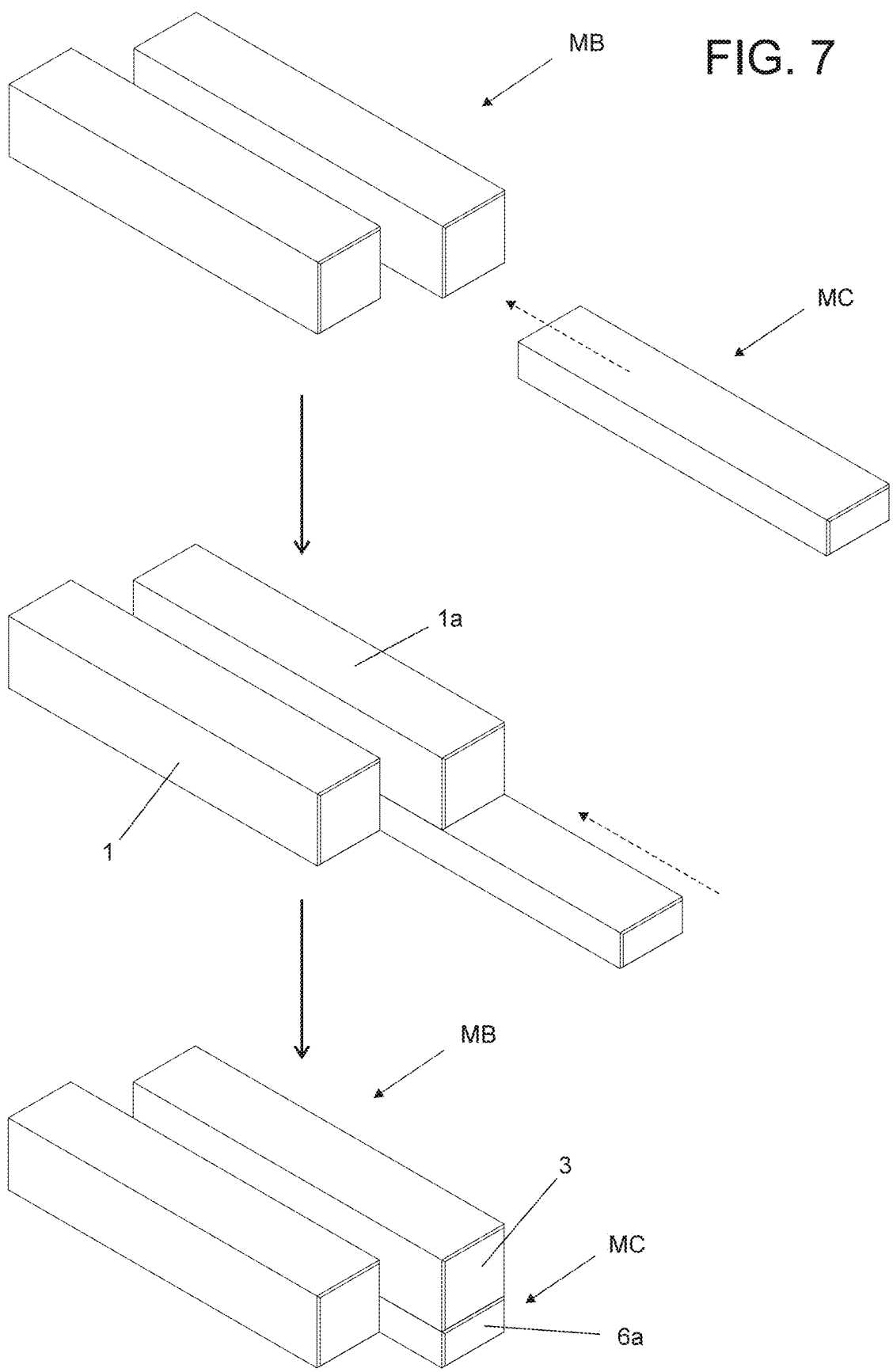

METALLIC MODULES AND ASSEMBLY SYSTEM FOR THE FORMATION OF SHIELDED WALLS, FLOOR AND CEILING FOR ROOMS USED FOR RADIOTHERAPY

BACKGROUND OF THE INVENTION

This description refers to a patent application for a pair of modules composed of metal blocks filled with a metallic powder, in a configuration that will allow several units of these modules to be attached together and welded to form shielded walls for radiotherapy rooms, with high capacity of attenuation of radiation.

The walls formed by these modules are easy and quick to assemble and do not show cracks, holes or fragmentation. The modules can also be used for repair or reinforcement of the radiotherapy area or room in a quick way and without the need of interdiction of the room for long periods of time both due to its capacity of shielding and due to the fact that its density is superior to that of the common concrete.

DESCRIPTION OF THE STATE OF THE ART

As is well known to those who have technical knowledge on the subject, in order to implement a Radiotherapy Service, it is necessary to choose and acquire equipment and elaborate a shielding project, within the stipulated standards so that the service obtains the necessary registrations and authorizations to its operation.

The Ministerial Order 1884/1994 of the Brazilian Ministry of Health determines that the service must comply with certain recommendations on protection of radiation and safety in radiotherapy, establishing the necessary requirements for the installation and operation of a radiotherapy service.

In an architectural design of radiation shielding for protection of radiation, the most common materials for the fabrication of the walls of the site are the concrete of normal density or of high density, steel plates and/or lead liners, being the common concrete the cheapest material and the most simple to use, but it has a low density compared to others, thus requiring a thick wall for the shield. If there is a space restriction, the use of alternative materials is considered. In some situations, especially when renovating a room, or in buildings close to very busy areas where space is critical, it may be necessary to use steel plates or a combination of steel and concrete in order to maintain the minimum thickness of the shielding and maximize the use of the room size. Although concrete is the most suitable material, it is essential to take special care in the wall frame, joints, launching sequence, vibration and curing of the concrete to avoid cracks, holes or dilatations.

Common concrete has the advantage of low cost and ease of construction, although concrete shields are quite thick. Concrete requires a metallic framing to increase resistance and molds for containment of fluid mass. High-density concrete can be used when there is a space limitation. However, its relatively high cost and the lack of appropriate attenuation curves contraindicate their regular use. Low carbon steel has appropriate shielding characteristics and, due to its strength, can also be used as a structural component. Steel plates can be used in addition to concrete when space is at the premium and also as a frame and shielding of doors and also as filling of recess in the walls. Lead is recommended as a shielding material for doors because although this material is denser than others, sheets or linings of lead are more expensive.

Just as an example, a picture from the internet has been chosen as FIG. 1 in the accompanying drawings, representing a cross-sectional view of a room shielded with concrete for linear accelerator, illustrating the thickness required for the walls.

Nowadays, this market has grown leaving a great gap between supply and need in the country. With increasing demand, radiotherapy equipment such as linear accelerator, perform treatments faster and on a larger scale. The problem here is that the shielding is not appropriate for the newer equipment and in a larger quantity. Usually, in an attempt to remedy such problems, adaptations are made with lead plates, iron or concrete, and in these cases, it is necessary to interdict the room during the period of the work to carry out the adjustments.

Objective of the Invention

In order to solve the above problems, the inventor has developed a pair of modules which consist of metal blocks filled with metal powder, preferably iron ore, in such a configuration to enable several units of these modules to be fitted together and welded, quickly and simply, for the formation of a wall, floor or ceiling with high radiation attenuation capacity and considerably less thickness when compared to concrete walls constructed for the same purpose. Thus, the walls formed by these modules are easy to construct, by the assembly, and do not have cracks, holes or fragmentation. This way, even when used for repair or strengthening of the radiotherapy area or room, the interdiction will not be necessary for long periods of time.

The material with which the modules are manufactured guarantees its low cost. Thus, even when modules manufactured in a larger size are used, in order to increase the shielding capacity of the wall, there is a big cost reduction on the project, especially compared to steel plates and, especially lead, ensuring the same shielding capacity, taking into account the appropriate density ratios.

DESCRIPTION OF THE DRAWINGS

As superficially explained, the blocks are best described in the accompanying drawings.

FIGS. 2 to 12 show the modules and their assembly and the reasons for this patent application:

FIG. 2 shows a perspective view of the base module, showing its blocks welded together in horizontal and vertical unevenness;

FIG. 3 shows the front view according to the previous figure;

FIG. 4 shows side view according to the previous figure;

FIG. 5 is a perspective view of the complementary module;

FIG. 6 is a cross-sectional view of one of the blocks of the base module, showing that the blocks are composed of a metal casing filled with metal powder or a composite blend;

FIG. 7 is a perspective view, in sequence, of a base module already on the ground and receiving a complementary module being slid below the block;

FIG. 8 is a view of a sequence of the previous figure, showing a second base module being brought close to the first one to be positioned behind it. The rear faces coinciding with the front faces of the second module, the latter receiving a complementary module underneath its displaced block, filling the space between the module and the floor;

FIG. 9 shows a vertical row already formed by the base modules on the floor, reaching the limit determined for the length of the wall to be formed. A second row is stacked over this first row of base modules, module by module, supporting its square block in the square block of the previous module and the block displaced in the block displaced from the previous module. The sequence shows that the stacking action described is repeated several times in a vertical stack until the desired height or horizontal width is reached, until the desired width of the walls, floor and/or ceiling is reached;

FIG. 10 shows the wall already built, with the desired height, thickness and length, then receiving a new base module unit positioned perpendicularly, being fitted in the space left by the displacement of the blocks. Details A, B, and C, in sequence, show this positioning and the introduction of the complementary module under the block displaced from this new perpendicular base module;

FIG. 11 shows the wall ready, with its perpendicular wall, both constituted of base modules and receiving a complementary module in the space left by the block displaced from each upper base module of the walls for alignment. The described walls were formed by only one layer of modules, but could have more layers, side by side, in order to be thicker;

FIG. 12 shows the two walls from the previous figure, now having received all the upper complementary modules, leveling them.

DETAILED DESCRIPTION OF THE INVENTION

Figure 1:
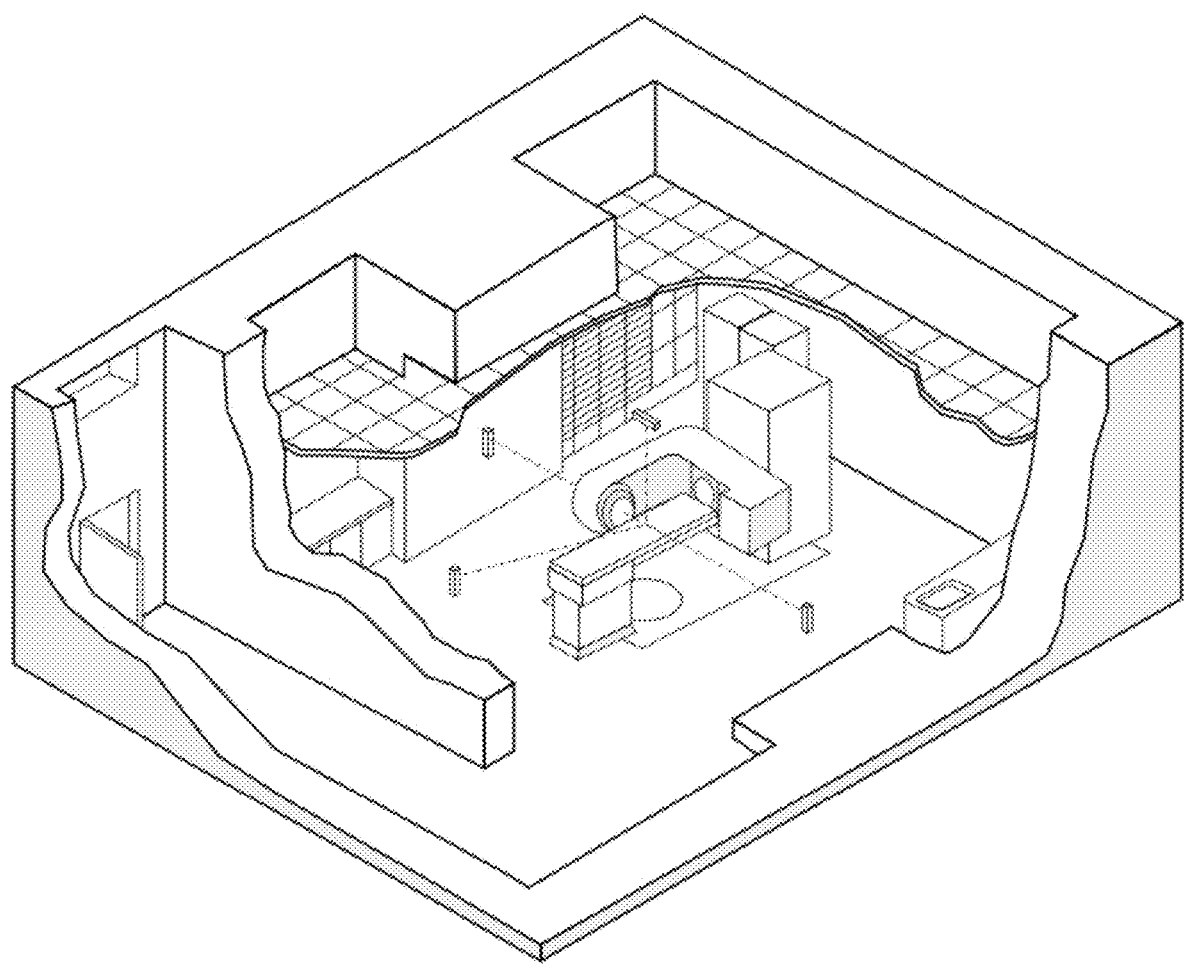
FIG. 1, shows the state of the art through a cross-sectional view of a room shielded with concrete for a linear accelerator.
Figure 8:
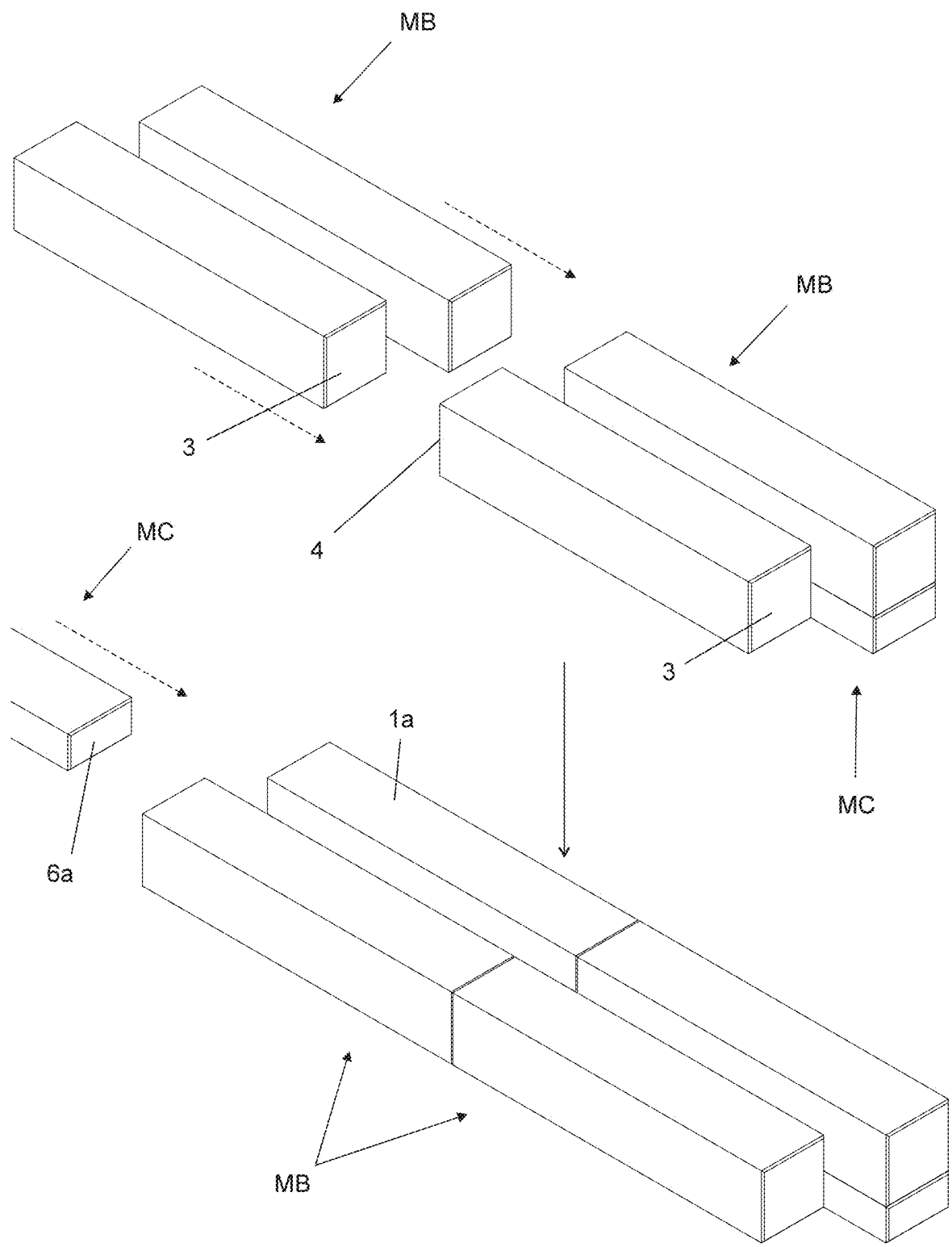
Figure 9:
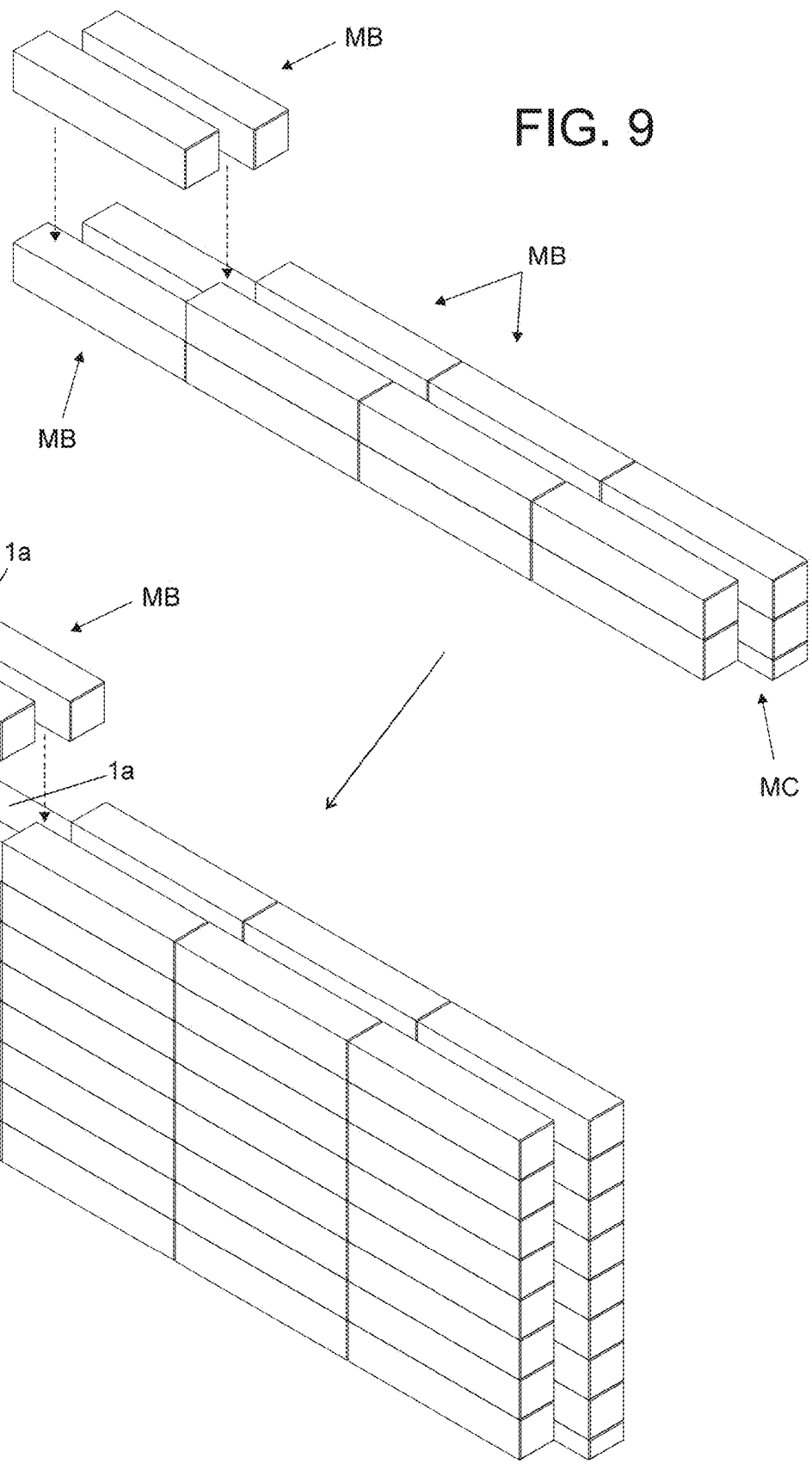
Figure 10:
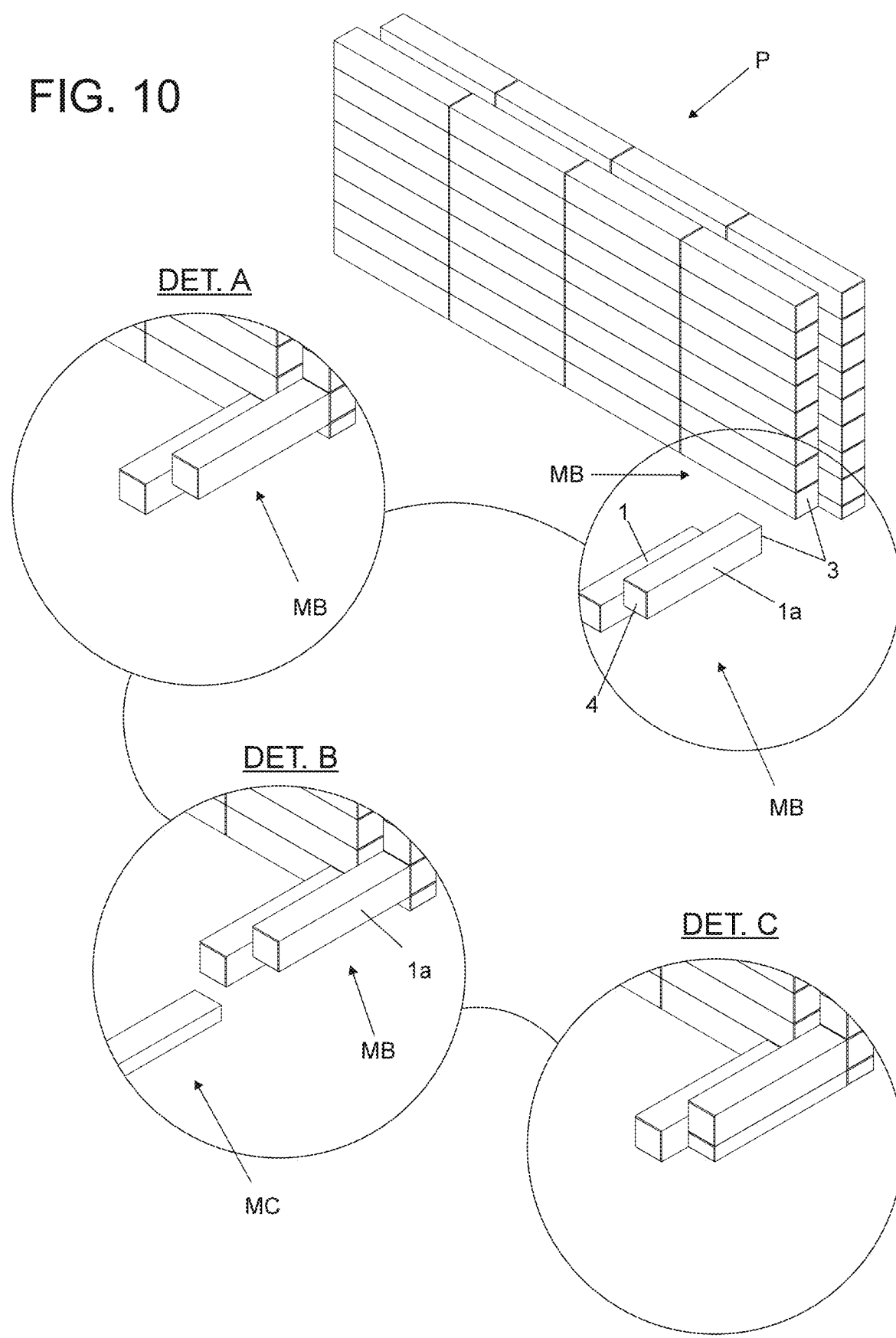
Figure 11:
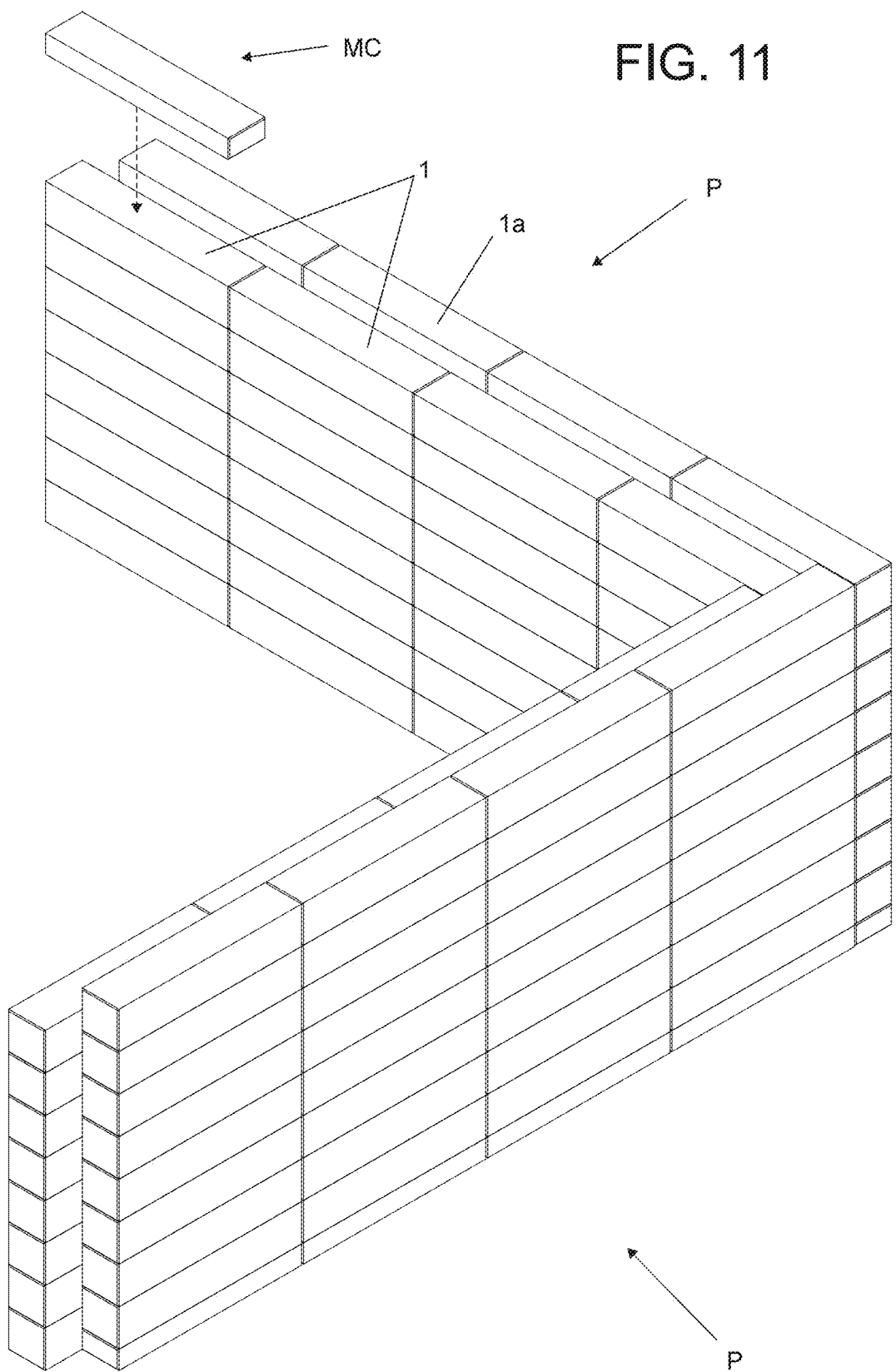
Figure 12:
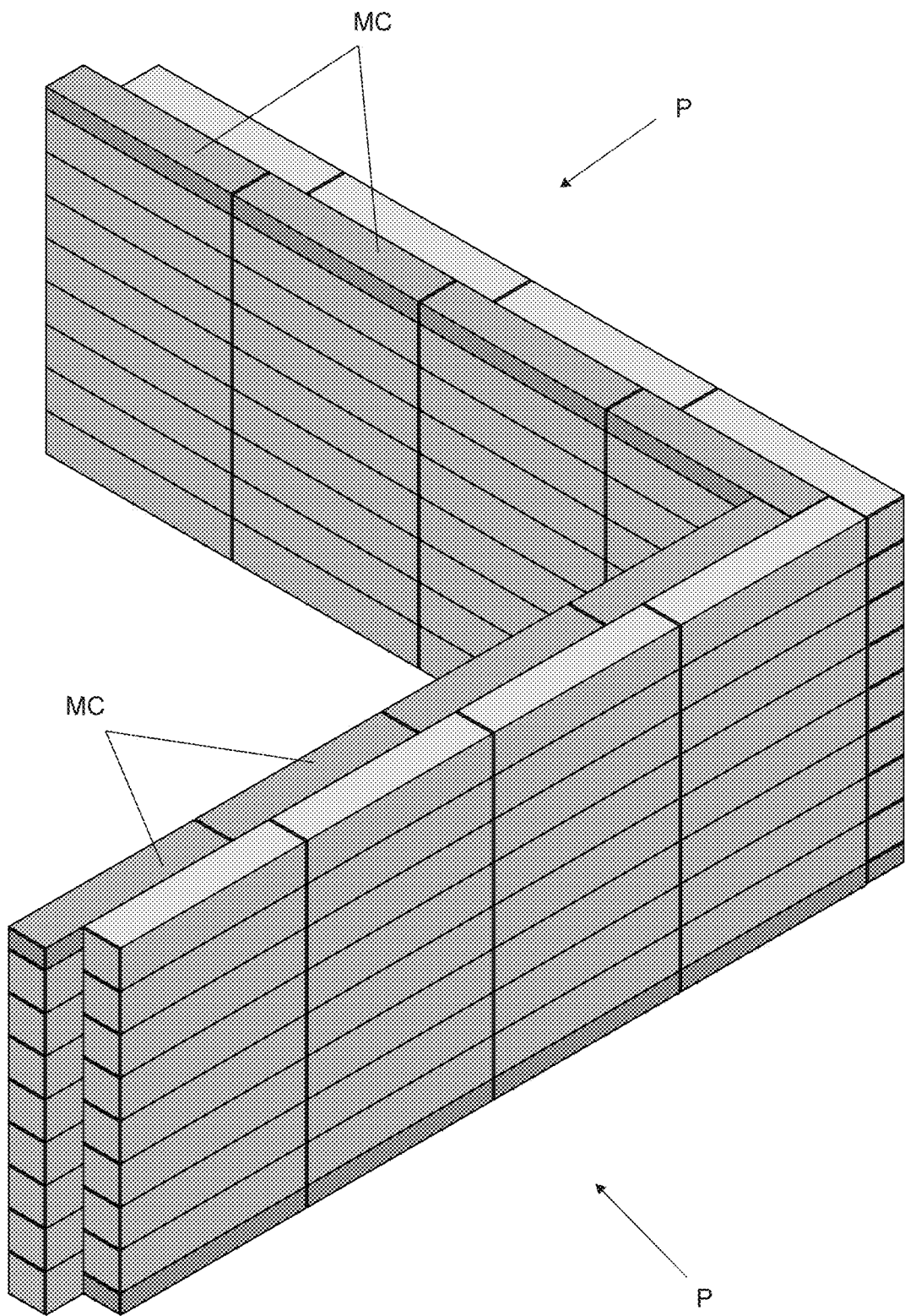

According to the attached figures, the metallic modules and assembly system for the formation of shielded walls, floor and ceiling for rooms used for radiotherapy object of this invention, is constituted by a square block (1), parallelepiped, that is, two equal sides and a stretched body (2), longitudinally projecting and spacing the front face (3) of the rear face (4), which have small bevels on the edges (5). On one side of its body (2), the square block (1) has a second block welded to it (1a), of equal configuration but displaced vertically exactly at the midpoint of the face of the first block previously mentioned (1) and horizontally, in the same dimension of one of its sides. This pair of blocks (1 and 1a) joined together as previously described, form a structure that will be referred to, herein, as the base module (MB) which will work with a complementary module (MC) which is formed by a rectangular parallelepiped block (6) having a width and length identical to the width and lengths of the square blocks (1 or 1a), but with a height exactly equal to half the height of the square block (1 or 1a) and the front (6a) and rear faces (6b) are also bordered by small bevels (5).

Blocks (1, 1a and 6) are high density and are formed by a metal casing (7) filled with metal powder (8), which may be iron ore, other derivative material or a blend, depending on the quality, and type of shielding to be achieved.

Thus, the modules (MB and MC) will form shielded walls with radioprotection for the radiotherapy area or room, to avoid leakage of ionizing radiation. To do so, with the floor of the area preferably already installed and properly finished, several units of base modules (MB) and complementary modules (MC) are brought to the site, according to the construction project. After demarcating the wall area, a first base module (MB) is placed on the floor with the square block facing down (1), then receiving a complementary module (MC) shim, inserted under its second block (1a), supporting it and making it firm, filling the lower space left by its vertically offset configuration misplaced compared to the first square block (1).

A new base module (MB) unit is then positioned behind the first one, matching and joining the rear faces (4) of the blocks (1 and 1a) with the front faces (3) of the blocks (1 and 1a) of the new unit, then a complementary module unit (MC) is being inserted underneath the second block (1a), supporting it. This action is repeated until the demarcated limit for the wall is reached, forming a pattern of unified modules (MB and MC) in a structure.

That way, a new base module (MB) unit is placed on top of the first, in the same position, joining the upper faces of the block (1) and the displaced block (1a) of the first unit with the respective lower faces of the block (1) and displaced block (1a) of this new base module unit (MB), stacking them vertically. This action is then repeated with all other units already positioned, linearly and horizontally and, after being positioned, these new units receive the stacking of more units of a base module (MB), vertically, until a solid wall (P) is obtained.

In this way, the first wall (P) is formed, a new base module unit (MB) is laid on the floor, perpendicular to the first one, where any of its blocks (1 or 1a) has its front face (3) or rear face (4) supported by the side face of the uneven block (1a) of the first base module (MB) of the wall (P) and its side face supported by the front face (3) of the block (1) of the latter. A complementary module unit (MC) is also inserted underneath the uneven block (1a) of the latter base module unit (MB) supporting it. Through the same process of stacking over the previous wall (P), this new perpendicular wall (P) is built and the same is done with the other walls (P), according to the project. Finally, on the upper part of the walls (P) a complementary module unit (MC) is positioned and fitted over each space left by the unevenness of the block (1) of the base module units (MB), leveling its surface and finishing, forming in each wall a monoblock consisting of several modules (MB and MC).

During the described assembly, each module unit (MB or MC) can be welded to the previous unit, acting as a mooring weld, for the perfect fixation and unification of the wall (P), which may also be formed by more than one row of modules (MB and MC), that is, a double wall, triple wall or as many rows as required for the desired shielding capacity. Besides being used to construct the walls (P) of the area to be protected against radiation leakage, the modules (MB and MC) can only be used as reinforcement of existing walls, floor, and ceiling of concrete or other material, when necessary.

For a person who has technical knowledge on the subject, it is clear that the walls (P) constituted by the modules (MB and MC) offer high capacity of shielding against radiation, since each block (1, 1a and 6), due to the construction method and the materials from which they are composed, can present density between 3.5 and 4 g cm$^{-3}$ compared to 2.35 g cm$^{-3}$ of the common concrete. Therefore, the required thickness of the walls (P) for the radiation insulation with the modules (MB and MC) will be considerably smaller than when constructed in common or dense concrete, while still maintaining a low cost for the project, very close to the use of concrete thanks to the low cost materials with which the modules (MB and MC) are manufactured. When required, the blocks (1, 1a and 6) of the modules (MB and MC) can be manufactured in larger scale, i.e., thicker, increasing the total density of the wall (P) and/or other shapes, different lengths or widths of each block (1, 1a and 6), however, maintaining its plug-in system and its module configuration (MB and MC).

It is also clear that, unlike walls made of concrete, they will not have cracks and suffer from premature wear due to the weather, requiring frequent repairs or reinforcing.

Finally, in addition to walls (P), the modules (MB and MC) presented here can be used for the construction of floors and ceilings, using the same pieces and the same system, but in horizontal assembly, achieving the same effect and shielding capability.

The invention claimed is:

1. A modular shielding structure for radiation protection in a radiotherapy room comprising:
    at least one wall structure comprising at least two rows;
    the first wall row comprising a row of base modules including first and second base modules aligned along a common longitudinal axis in a sliding relationship such that a front face of a first base module and a rear face of a second base module abut, where further base modules are arranged to maintain the pattern of face abutment established by the first and second base modules until a row of predetermined length and where a bottom row of complementary modules are positioned to fill any gap on a lower side of a base module row;
    second and subsequent wall rows comprising the arrangement of the first wall row placed on top of or adjacent to the first wall row successively and up to a desired wall height such that bottom surfaces of second or subsequent wall rows abut top surfaces of a preceding wall row;
    a second wall base module aligned such that a longitudinal axis of the second wall base module is perpendicular to that of a wall base module located in a lower corner of the wall;
    a front face of a second wall base module is contacting a first top row of complementary modules filling a gap on an upper side of a wall top; and
    wherein, said base modules comprise two identical cuboids fused together, each of these cuboids having equally sized front and rear faces connected with four rectangular sides comprising left, right, top, and bottom sides and being positioned in parallel, side-by-side, along mutually facing rectangular side and where the cuboids are also mutually offset vertically and horizontally; and
    wherein, said complementary modules comprise a single cuboid having equally sized rectangular front and rear faces connected with four rectangular sides comprising left, right, top, and bottom sides, the complementary modules having top and bottom edges equal in length to the length of the edges of base module faces and side edges one half the length of the edges base module faces, and the complementary modules comprise top and bottom sides equal in dimension to the dimensions of the sides of base module cuboids, left and right sides with length equal to the lengths of complementary module top and bottom sides, and widths equal to the dimension of side edges of complementary module faces.

2. The modular shielding structure of claim 1, further comprising second wall structure, the second wall structure comprising plural base modules and plural complementary modules, the second wall structure arranged perpendicular a first wall structure and comprising second wall structure base modules perpendicular the first wall structure base modules and in contact with first wall base modules such that the second wall structure base module faces abut the sides of the first wall base modules; and
    wherein the second wall structure comprises the same components and basic arrangement of the wall structure of claim 1 such that the second wall structure is composed of sufficient base modules and complementary modules to have a desired height.

3. The modular shielding structure of claim 1 further comprising each of said modules and complementary modules are made of metal casing and filled internally with metal powder.

* * * * *